(12) United States Patent
Fukazu et al.

(10) Patent No.: US 11,937,966 B2
(45) Date of Patent: Mar. 26, 2024

(54) RADIATION IMAGING CONTROL APPARATUS, RADIATION IRRADIATING PARAMETER DETERMINING METHOD, AND STORAGE MEDIUM

(71) Applicant: Konica Minolta, Inc., Tokyo (JP)

(72) Inventors: Kosuke Fukazu, Hino (JP); Naoki Hayashi, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/347,988

(22) Filed: Jun. 15, 2021

(65) Prior Publication Data

US 2021/0393232 A1 Dec. 23, 2021

(30) Foreign Application Priority Data

Jun. 17, 2020 (JP) .................................. 2020-104144

(51) Int. Cl.
*A61B 6/00* (2006.01)
*A61B 6/46* (2024.01)

(52) U.S. Cl.
CPC .............. *A61B 6/545* (2013.01); *A61B 6/465* (2013.01); *A61B 6/56* (2013.01)

(58) Field of Classification Search
CPC ........... A61B 6/465; A61B 6/54; A61B 6/545; A61B 6/56; G16H 30/20; G16H 30/40; G16H 40/60
See application file for complete search history.

(56) References Cited

U.S. PATENT DOCUMENTS

| 6,859,513 B2* | 2/2005 | Sako ........................ A61B 6/00 378/8 |
| 8,538,776 B2* | 9/2013 | Reiner .................... A61B 6/542 600/300 |
| 2011/0052034 A1* | 3/2011 | Watanabe ............. G06T 7/0012 378/115 |

(Continued)

FOREIGN PATENT DOCUMENTS

| JP | 2014000131 A | 1/2014 |
| JP | 2015084938 A | 5/2015 |
| JP | 2019048005 A | 3/2019 |

OTHER PUBLICATIONS

Notice of Reasons for Refusal for corresponding JP Application No. 2020-104144; dated Nov. 14, 2023.

*Primary Examiner* — Dani Fox
*Assistant Examiner* — Soorena Kefayati
(74) *Attorney, Agent, or Firm* — CANTOR COLBURN LLP (57) ABSTRACT

A radiation imaging control apparatus includes a hardware processor and an operator. The hardware processor obtains an examination order and one or a plurality of radiation irradiating parameters corresponding to each examination order. The examination order to be executed is selected using the operator. When the examination order is selected on the operator, the hardware processor determines a selecting condition according to a priority setting from a plurality of selecting conditions, and selects a radiation irradiating parameter for the examination order from one or a plurality of radiation irradiating parameters according to the determined selecting condition.

9 Claims, 9 Drawing Sheets

(56) References Cited

U.S. PATENT DOCUMENTS

| | | | | |
|---|---|---|---|---|
| 2012/0183191 A1* | 7/2012 | Nakamura | ............ | G16H 30/40 |
| | | | | 382/128 |
| 2012/0278359 A1* | 11/2012 | Igarashi | ................ | G16H 50/20 |
| | | | | 707/769 |
| 2013/0266118 A1* | 10/2013 | Senba | .................... | A61B 6/463 |
| | | | | 378/62 |
| 2013/0279787 A1* | 10/2013 | Watanabe | ............ | A61B 6/465 |
| | | | | 382/132 |
| 2014/0177798 A1* | 6/2014 | Kitagawa | ................ | A61B 6/56 |
| | | | | 378/62 |
| 2015/0063542 A1* | 3/2015 | Park | ...................... | A61B 6/542 |
| | | | | 378/62 |
| 2015/0272703 A1* | 10/2015 | Arima | ................... | A61B 6/548 |
| | | | | 378/62 |
| 2016/0015340 A1* | 1/2016 | Nenoki | ................. | A61B 6/468 |
| | | | | 378/98 |
| 2016/0166227 A1* | 6/2016 | Tanaka | .................. | A61B 6/563 |
| | | | | 382/132 |
| 2016/0228081 A1* | 8/2016 | Inoue | .................... | A61B 6/465 |
| 2016/0278729 A1* | 9/2016 | Iijima | ..................... | A61B 6/54 |
| 2016/0287202 A1* | 10/2016 | Miyachi | .............. | A61B 6/4266 |
| 2017/0163869 A1* | 6/2017 | Semba | ............ | H04N 21/42204 |
| 2017/0300358 A1* | 10/2017 | Rahme | ................ | G06F 16/5866 |
| 2017/0360390 A1* | 12/2017 | Tajima | ................... | A61B 6/548 |
| 2018/0218785 A1* | 8/2018 | Sugiyama | .............. | A61B 6/037 |
| 2018/0330286 A1* | 11/2018 | Ramanathan | .......... | G16H 30/20 |
| 2019/0046139 A1* | 2/2019 | Hattori | .................. | A61B 6/563 |
| 2019/0076109 A1* | 3/2019 | Uehara | .................. | G01T 1/161 |
| 2019/0159746 A1* | 5/2019 | Hikosaka | ............. | A61B 6/465 |
| 2019/0189270 A1* | 6/2019 | Ishii | ...................... | G16H 50/30 |
| 2019/0198159 A1* | 6/2019 | Hegde | ................ | A61B 6/5217 |
| 2020/0243177 A1* | 7/2020 | Terai | .................... | G16H 15/00 |
| 2021/0121146 A1* | 4/2021 | Inomata | ................. | A61B 6/467 |

\* cited by examiner

| No. | PARAMETER NAME |
|---|---|
| 1 | TUBE VOLTAGE(kV) |
| 2 | TUBE CURRENT(mA) |
| 3 | EXPOSURE DURATION(msec) |
| 4 | EXPOSURE AMOUNT(mAs) |
| 5 | SETTING MODE |
| 6 | FOCAL SIZE |
| 7 | PHOTO TIMER(AEC) |
| 8 | COLLIMATOR SIZE |
| 9 | FILTER |
| 10 | WS (STANDING/LYING) |
| 11 | TUBE |
| 12 | PHYSIQUE |
| 13 | IRRADIATING FIELD SIZE |
| 14 | GRID MOUNTING STATE |
| 15 | SID |

FIG. 4

| FIRST SELECTING CONDITION | CONDITION | | SECOND SELECTING CONDITION | CONDITION | | FINAL DETERMINATION |
|---|---|---|---|---|---|---|
| | APR CODE | ⇑ | ⇑ | ⇑ | ⇑ | PRESET INITIAL DATA SET |
| LINKING SETTING | IRRADIATING PARAMETER NOTIFYING COMMAND EXISTS | ⇑ | WHETHER NOTIFICATION FROM X-RAY GENERATING APPARATUS EXISTS | NOTIFICATION EXISTS | ⇑ | FINAL DATA SET RECEIVED FROM X-RAY GENERATING APPARATUS |
| | | | | NO NOTIFICATION | ⇑ | DATA SET OF PREVIOUS IMAGING |
| | NO IRRADIATING PARAMETER NOTIFYING COMMAND | ⇑ | WHETHER CHANGE IN IMAGING CONTROL APPARATUS SIDE EXISTS | CHANGE EXISTS | ⇑ | DATA SET CHANGED IN IMAGING CONTROL APPARATUS |
| | | | | NO CHANGE | ⇑ | DATA SET OF PREVIOUS IMAGING |
| | IMAGING CONTROL APPARATUS SIDE PRIORITIZED | ⇑ | CONTENTS OF FINAL UPDATE | CHANGE IN IMAGING CONTROL APPARATUS | ⇑ | DATA SET CHANGED IN IMAGING CONTROL APPARATUS |
| | | | | CHANGE IN X-RAY GENERATING APPARATUS | ⇑ | FINAL DATA SET RECEIVED FROM X-RAY GENERATING APPARATUS |
| | | | | NO CHANGE | ⇑ | PRESET INITIAL DATA SET |
| ENVIRONMENT SETTING | X-RAY GENERATING APPARATUS SIDE PRIORITIZED | ⇑ | WHETHER CHANGE IN X-RAY GENERATING APPARATUS SIDE EXISTS | CHANGE EXISTS | ⇑ | FINAL DATA SET RECEIVED FROM X-RAY GENERATING APPARATUS |
| | | | | NO CHANGE | ⇑ | PRESET INITIAL DATA SET |
| IMAGING PERFORMED AGAIN DUE TO FAILURE | PASS ON IRRADIATING PARAMETER OF FAILURE TARGET | ⇑ | WHETHER CHANGE IN X-RAY GENERATING APPARATUS SIDE EXISTS | CHANGE EXISTS | ⇑ | FINAL DATA SET RECEIVED FROM X-RAY GENERATING APPARATUS |
| | | | | NO CHANGE | ⇑ | DATA SET OF PREVIOUS IMAGING |

–IRRADIATING PARAMETER TRANSMITTED TO X-RAY GENERATING APPARATUS

| PRIORITY | DETERMINING STANDARD |
|---|---|
| 1 | PRESET VALUE |
| 2 | LAST VALUE CHANGED IN X-RAY GENERATING APPARATUS |
| 3 | LAST VALUE CHANGED IN IMAGING CONTROL APPARATUS |

FIG. 7

RADIATION IMAGING CONTROL APPARATUS, RADIATION IRRADIATING PARAMETER DETERMINING METHOD, AND STORAGE MEDIUM

CROSS-REFERENCE TO RELATED APPLICATIONS

The present invention claims priority under 35 U.S.C. § 119 to Japanese Patent Application No 2020-104144 filed on Jun. 17, 2020 is incorporated herein by reference in its entirety.

BACKGROUND

Technological Field

The present invention relates to a radiation imaging control apparatus, a radiation irradiating parameter determining method, and storage medium.

Description of the Related Art

Conventionally, in the field of medicine, the image diagnosis using the X-ray imaging system is performed. Lately, due to the development of a flat panel detector (FPD) which generates an X-ray image based on incident X-ray, the method of diagnosis by X-ray dynamic imaging is becoming established. In the X-ray dynamic imaging, in addition to shape information of respiratory organs and circulatory organs, dynamic information can be obtained from the change in the pixel value (density) of the X-ray image. With this, for example, chest portion dynamic diagnosis of a lung ventilation function, pulmonary blood flow, and the like can be performed.

Usually, an X-ray imaging system includes an X-ray generating apparatus that generates X-rays and irradiates the X-ray to the subject, and an X-ray imaging apparatus that images the X-ray image based on an incident dose of X-ray transmitting through the subject.

The X-ray generating apparatus includes an X-ray tube apparatus which irradiates X-rays to the subject, a high voltage generating apparatus which applies voltage to the X-ray tube apparatus, an X-ray generating control apparatus which controls the operation of the X-ray tube apparatus and high voltage generating apparatus, an X-ray generating console to input and confirm the irradiating parameter, etc., and an irradiating switch to instruct irradiating of the X-ray.

The X-ray imaging apparatus includes an FPD which detects the X-ray transmitted through the subject, converts the X-ray to image data and outputs the image data, an imaging control apparatus which controls the operation of the FPD and performs a predetermined process (for example, image processing and display control processing) on the obtained X-ray image data, and an imaging console which performs input and confirmation of the imaging conditions. The imaged X-ray image is displayed on the imaging console.

In the X-ray imaging system, when the X-ray imaging is performed, the irradiating parameter of the radiation is set in advance according to the examination order. Normally, the irradiating parameter is set through the X-ray generating console. Lately, the X-ray generating apparatus and the X-ray imaging apparatus are linked. With this, when an instruction is input to execute the examination order in the X-ray imaging apparatus, the irradiating parameter set in advance according to the contents of imaging in the examination order is automatically set in the X-ray generating apparatus.

The linking of the imaging condition between the X-ray imaging apparatus and the X-ray generating apparatus is performed by specifying an imaging condition table number of the X-ray generating apparatus (condition anatomical in the X-ray generating apparatus) or transmitting the imaging condition (kV, mA, ms, mAs, AEC, type of operation (standing, lying), irradiating field) from the X-ray imaging apparatus.

The imaging condition table number or the imaging condition parameter is associated with the examination order in advance, and the imaging condition in which the order is selected when the imaging is performed is automatically transmitted to the X-ray generating apparatus, and with this, the linking condition is transmitted.

There are several methods to decrease the burden of the person who performs the imaging regarding the method of handling and transmitting the parameters of the preset imaging condition.

For example, if the examination order with the same site and same direction in the same group continues, only the imaging condition in the examination order which is ahead are transmitted, and the imaging condition in the examination order which is later is not transmitted (JP 2014-131).

Alternatively, when a plurality of imaging is performed, it is determined whether to transmit the imaging condition of the next examination order depending on whether the imaging condition is changed (JP 2019-48005).

SUMMARY

According to the above prior art, the irradiating parameter is specified on the X-ray generating apparatus side or is only preset in advance. However, lately, due to diagnosis cars and an X-ray system in an all-in-one style, there are cases where it is necessary to change the irradiating parameters in the imaging control apparatus side. The prior art is silent regarding such configuration.

Moreover, the transmitting of the irradiating parameter when the imaging is performed successively is to be the problem to be solved and the problems for the case in which the imaging target is switched many times for a plurality of orders are not shown.

For example, generally, the irradiating parameter is linked to the examination order, and the preset data is transmitted to the X-ray generating apparatus side each time the examination order is switched on the screen on the imaging control apparatus side.

Turning to JP 2014-131, the disclosure only shows that the irradiating parameter is not transmitted in the same group and makes no judgement regarding whether or not there is change.

Moreover, J P 2019-48005 describes the irradiating parameter is transmitted without any conditions when the imaging is performed for the first time, and does not consider changing the order of imaging and the imaging conditions in the beginning. Therefore, it is not possible to cope with the situation when the irradiating parameter is changed in this term.

Due to values set in advance such as linked irradiating parameters using the APR (anatomical program) code, there is an environment in which the change on the X-ray imaging control apparatus side cannot be reflected. Therefore, it is not possible to cope with operation regarding such connection.

The present invention is made in view of the above problems, and the purpose of the present invention is to provide a radiation imaging control apparatus, a radiation irradiating parameter determining method, and storage medium which are capable of selecting a suitable irradiating parameter of radiation for an examination order.

To achieve at least one of the abovementioned objects, according to an aspect of the present invention, a radiation imaging control apparatus reflecting one aspect of the present invention is shown, the apparatus including a hardware processor; and an operator, wherein, the hardware processor obtains an examination order and one or a plurality of radiation irradiating parameters corresponding to each examination order, the examination order to be executed is selected using the operator, and when the examination order is selected on the operator, the hardware processor determines a selecting condition according to a priority setting from a plurality of selecting conditions, and selects a radiation irradiating parameter for the examination order from one or a plurality of radiation irradiating parameters according to the determined selecting condition.

A radiation irradiating parameter determining method including: obtaining an examination order and one or a plurality of radiation irradiating parameters corresponding to each examination order, selecting the examination order to be executed, and when the examination order is selected, determining a selecting condition according to a priority setting from a plurality of selecting conditions, and selecting a radiation irradiating parameter for the examination order from one or a plurality of radiation irradiating parameters according to the determined selecting condition.

A non-transitory computer-readable storage medium storing a program causing a computer to perform: obtaining an examination order and one or a plurality of radiation irradiating parameters corresponding to each examination order, selecting the examination order to be executed, and when the examination order is selected, determining a selecting condition according to a priority setting from a plurality of selecting conditions, and selecting a radiation irradiating parameter for the examination order from one or a plurality of radiation irradiating parameters according to the determined selecting condition.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Embodiments of the present invention are described with reference to the drawings.

Various preferable technical limits are applied to the embodiments to implement the invention, but the technical scope of the present invention is not limited to the embodiments described below and the illustrated examples.

Figure 1:
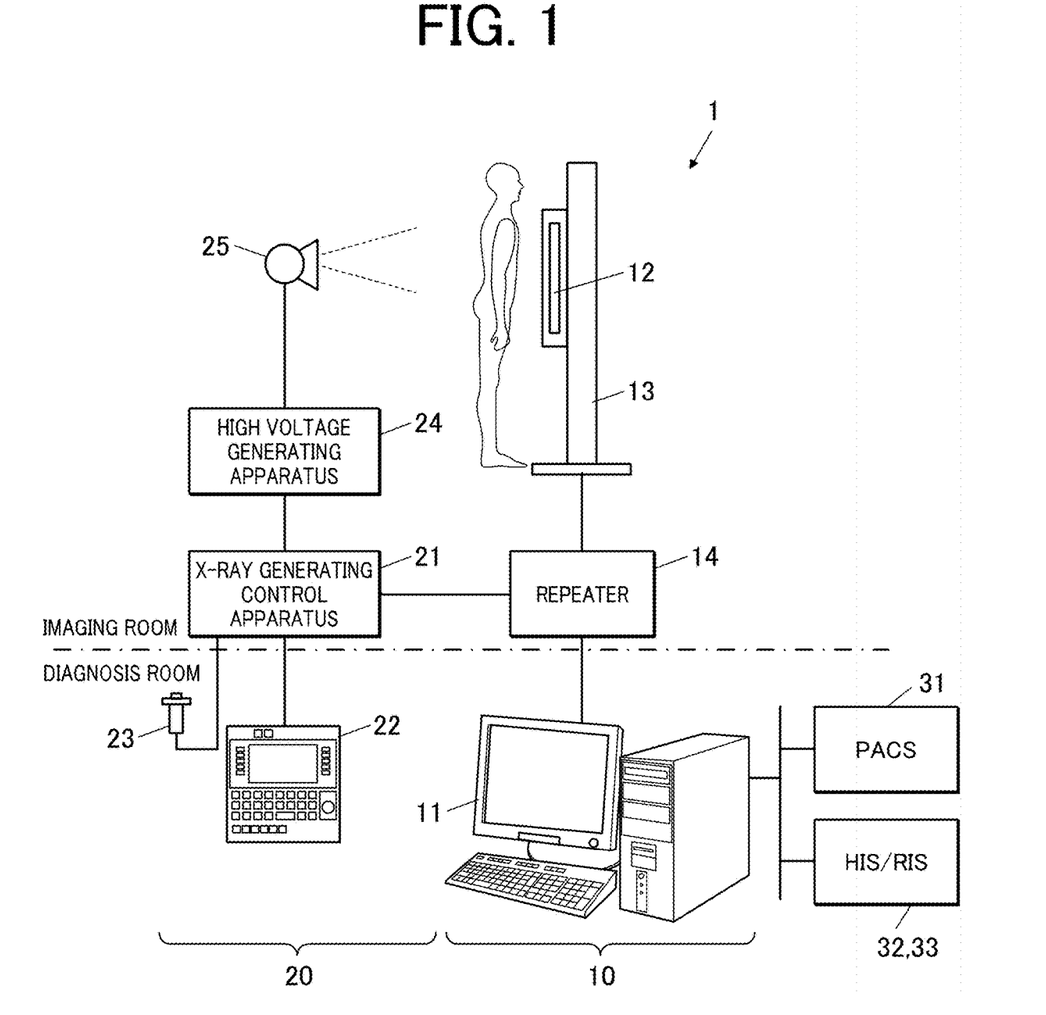
FIG. 1 is a diagram showing an X-ray imaging system regarding an embodiment of the present invention.

FIG. 1 is a diagram showing an X-ray imaging system 1 according to an embodiment of the present invention.

The X-ray imaging system 1 is a combined imaging system in which signals are communicated between an X-ray generating apparatus 20 and an X-ray imaging apparatus 10, and X-ray imaging is performed while linking the above.

As shown in FIG. 1, the X-ray imaging system 1 includes the X-ray imaging apparatus 10 and the X-ray generating apparatus 20.

The X-ray imaging system 1 is connected to a Picture Archiving and Communication System (PACS) 31, a Hospital Information System (HIS) 32, and a Radiology Information System (RIS) 33 through a communication network.

The information is transmitted and received according to a DICOM (Digital Imaging and Communications in Medicine) standard, for example, in the communication network including the X-ray imaging system 1, the PACS 31, the HIS 32, and the RIS 33.

The X-ray imaging apparatus 10 includes an imaging control apparatus 11, a FPD 12, an imaging stand 13, and a repeater 14.

The X-ray imaging apparatus 10 visualizes the X-ray transmitted through an imaging target site such as the chest portion or the stomach portion, and images an X-ray image showing a state inside the body.

The FPD 12 is an imaging apparatus which detects the X-ray which is irradiated from an X-ray tube apparatus 25 transmitted through the subject, and outputs the X-ray image data.

For example, the FPD 12 is attached to the imaging stand 13 and the FPD 12 is connected to be able to communicate with the imaging control apparatus 11 through the imaging stand 13 and the repeater 14 by wired communication.

The FPD 12 may be connected with the imaging control apparatus 11 by wireless communication. When the FPD 12 includes the wireless communication function, in addition to attaching the FPD 12 to the dedicated imaging stand 13, the FPD 12 can be used by placing the FPD 12 on the bed where the subject lies or by allowing the subject to hold the FPD 12.

For example, the FPD 12 includes a scintillator which converts the incident X-ray to light, a photodiode (PD) positioned in a matrix corresponding to a pixel, and a TFT (Thin Film Transistor) positioned corresponding to the PDs (all are not illustrated).

The incident X-ray is converted to light by the scintillator, the light enters the PD and is accumulated as charge for each pixel. The charge accumulated in the PD flows out through the TFT switch and the signal line, and is amplified. A/D conversion is performed on the charge. With this, the charge is output to the imaging control apparatus 11 as X-ray image data.

The FPD 12 can be a non-direct conversion type as described above or can be a direct conversion type which directly converts the X-ray to the electric signal.

The imaging stand 13 holds the FPD 12 detachably so that an X-ray incident surface of the FPD 12 faces the X-ray tube apparatus 25. As the imaging stand 13, FIG. 1 shows a standing position imaging stand in which the subject is imaged in a standing position.

The imaging stand 13 may be an imaging stand for a lying position in which the subject is imaged in a lying position.

For example, the imaging stand 13 is connected to be able to communicate with the imaging control apparatus 11 through the repeater 14 by wired communication.

The imaging control apparatus 11 is linked with the X-ray generating control apparatus 21 and controls the radiation imaging system 1. For example, the imaging control apparatus 11 transmits a detection condition to the FPD 12 and sets the detection condition. The detection condition includes image size to be imaged, frame rate (dynamic imaging), and information regarding the signal process performed by the FPD 12 (for example, gain of the amplifier). The imaging control apparatus 11 controls the operations of the FPD 12, obtains the X-ray image data from the FPD 12, performs predetermined image processing on the X-ray image data and displays the image on a display 113 (see FIG. 2).

The imaging control apparatus 11 functions as a radiation imaging control apparatus according to the present invention. The details of the imaging control apparatus 11 is described later.

The imaging control apparatus 11 may be a portion of the X-ray generating apparatus 20. For example, the imaging control apparatus 11 includes the function as an X-ray generating console 22 of the X-ray generating apparatus 20 (that is, a combined X-ray imaging system).

The X-ray generating apparatus 20 includes the X-ray generating control apparatus 21, the X-ray generating console 22, an irradiating switch 23, a high voltage generating apparatus 24, and an X-ray tube apparatus 25.

The X-ray tube apparatus 25 is positioned in a position facing the FPD 12 with the subject in between. When the high voltage is applied to the X-ray tube apparatus 25 by the high voltage generating apparatus 24, the X-ray is generated and the X-ray is irradiated to the subject. The X-ray tube apparatus 25 includes an X-ray movable focus which adjusts the irradiating field of the X-ray.

The X-ray generating console 22 and the irradiating switch 23 are connected to the X-ray generating control apparatus 21 through the signal cable.

The X-ray generating console 22 is an operation table to perform input of the irradiating parameter and the like. The irradiating switch 23 is a switch to instruct the irradiating of the X-ray, and includes a press button switch which is pressed in two stages and which returns automatically. In the irradiating switch 23, when the first stage of pressing is performed, the warmup start signal to start warmup of the X-ray tube apparatus 25 is transmitted to the X-ray generating control apparatus 21, and when the second stage of pressing is performed, the irradiating start signal to allow the X-ray tube apparatus 25 to start irradiating of the X-ray is transmitted to the X-ray generating control apparatus 21.

Figure 3:
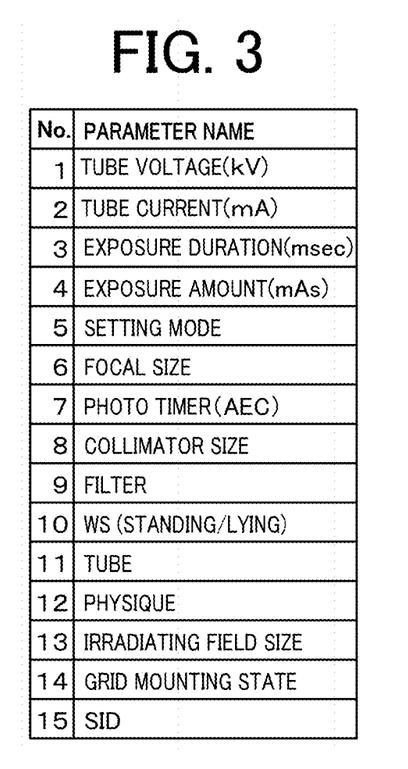
FIG. 3 is a diagram showing a list of a parameter used to link the imaging control apparatus and the X-ray generating apparatus.

Based on the irradiating parameter from the X-ray generating console 22 (radiation irradiating parameter) and the control signal from the irradiating switch 23 (warmup start signal and irradiating start signal), the X-ray generating control apparatus 21 controls the operation of the high voltage generating apparatus 24 and the X-ray tube apparatus 25. For example, as shown in FIG. 3, the irradiating parameter includes a plurality of parameters such as a tube voltage, a tube current, an exposure duration, an exposure amount, a setting mode, a focal size, a photo timer (AEC), a collimator size, a filter type, an imaging posture (WS) (standing/lying), tube, physique, irradiating field size, grid mounting state, SID, and the like.

The irradiating parameter can be set through the X-ray generating console 22. The irradiating parameter can be set using the imaging control apparatus 11.

Specifically, when the X-ray imaging apparatus 10 is linked with the X-ray generating apparatus 20, if the instruction to execute the examination order is made in the imaging control apparatus 11, the irradiating parameter is selected based on a priority rule, and the irradiating parameter is transmitted to the X-ray generating control apparatus 21 and set. The user can finely adjust the irradiating parameter through the X-ray generating console 22.

Figure 2:
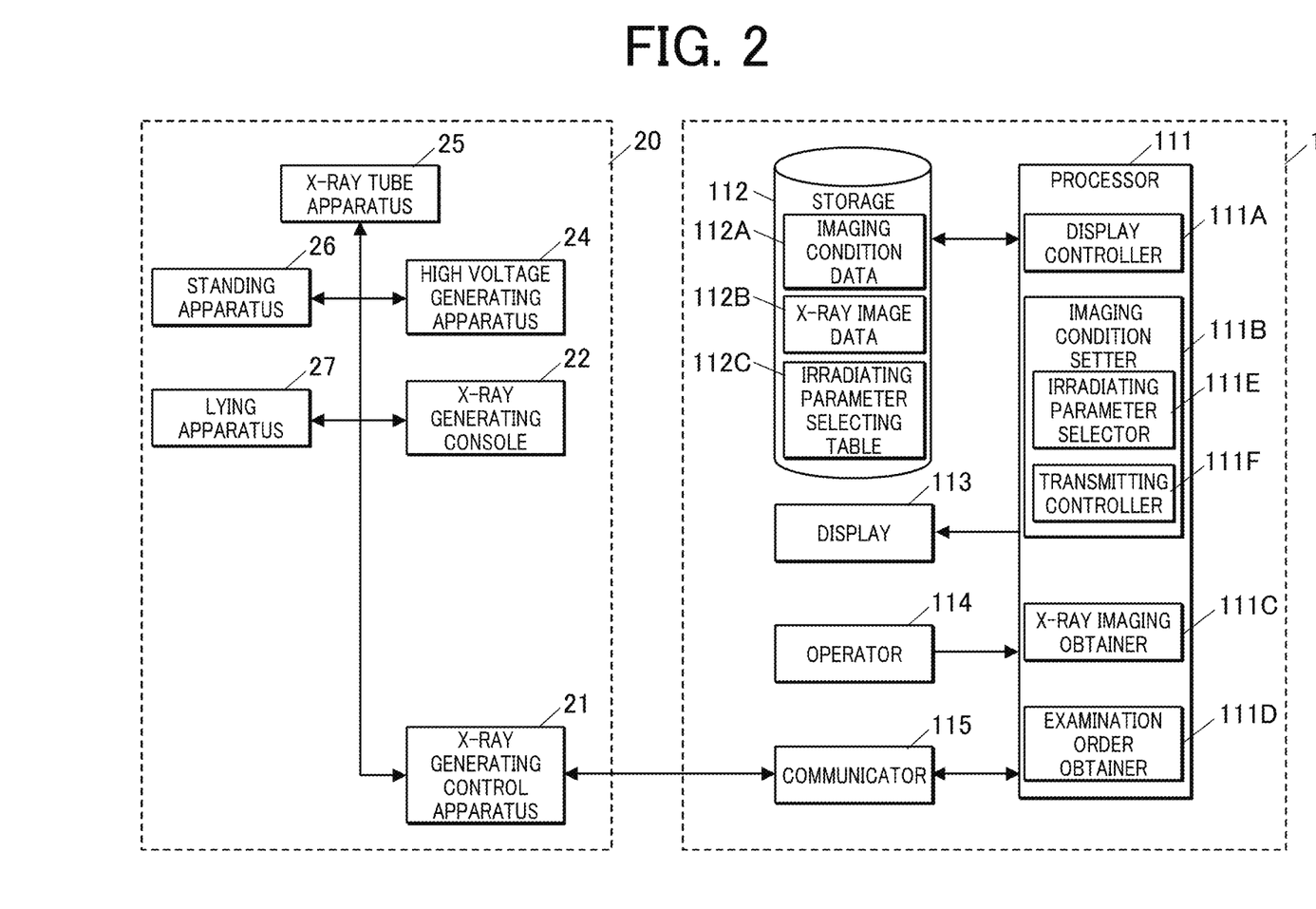
FIG. 2 is a diagram showing a configuration of an imaging control apparatus and an X-ray generating apparatus.

FIG. 2 is a diagram showing a configuration of the imaging control apparatus 11 and the X-ray generating apparatus 20. As shown in FIG. 2, the imaging control apparatus 11 includes a processor 111, a storage 112, a display 113, an operator 114, and a communicator 115.

The processor 111 includes a Central Processing Unit (CPU) as a calculating/control apparatus a Read Only Memory (ROM) and a RAM (Random Access Memory) as main storage apparatuses, and the like (all not shown). Basic programs and basic setting data are stored in the ROM. The CPU reads the program according to the processing contents from the ROM or the storage 112, and deploys the above in the RAM. By executing the deployed program, the operation of the FPD 12, etc. is centrally controlled. According to the present embodiment, the processor 111 executes the irradiating parameter setting process for the X-ray imaging and effectively reduces the burden of operation on the user when the irradiating parameter of the X-ray generating apparatus 20 is set.

The storage 112 is an auxiliary storage apparatus such as a Hard Disk Drive (HDD) or a Solid State Drive (SSD). The storage 112 may be a disc drive which drives an optical disc such as a Compact Disc (CD), Digital Versatile Disc (DVD), or a magneto optical disk and reads and writes the information. For example, the storage 112 may be a memory card such as a USB memory, SD card or the like.

The storage 112 stores various programs executed in the processor 111, parameters necessary to execute the programs, and data including the processing results. The storage 112 stores imaging condition data 112A and X-ray image data 112B, for example. The imaging condition data 112A includes data of the irradiating parameter in the X-ray generating apparatus 20 and the data of the detection condition in the FPD 12.

For example, the imaging condition is associated with the imaging contents (imaging site, imaging direction, body shape of subject, etc.) including the examination order.

An irradiating parameter selecting table 112C which determines a priority rule for selecting the irradiating parameter is stored in the storage 112. The irradiating parameter selecting table 112C is described in detail later.

For example, the display 113 includes a flat panel display such as a liquid crystal display, an organic EL display, and the like. Based on the display control signal from the processor 111, the display 113 displays the contents of the examination order and the imaged X-ray image. The examination order includes patient information of the patient as the subject (for example, patient ID, patient name, birthday, sex), posture information in imaging (for example, posture (standing/lying), irradiating direction (back/front/side), imaging site information (for example, chest portion), examination item (lung ventilation function, lung blood flow), and examination history of subject (imaging condition of previous examination)).

The operator 114 includes a keyboard including cursor keys, numeric input keys, and various function keys, and a pointing device such as a mouse. The operator 114 receives the operation signal input by key operation or mouse operation, and outputs the operation signal to the processor 111. For example, the user is able to input the imaging condition including the irradiating parameter through the operator 114.

The operator 114 is used when the examination order is selected and functions as an order selector.

For example, the display 113 and the operator 114 may be formed as one as in a flat panel display including a touch panel.

The communicator 115 is a communication interface such as a Network Interface Card (NIC), a Modulator-Demodulator (MODEM), a Universal Serial Bus (USB), and the like.

The processor 111 transmits and receives various information according to the DICOM standard with apparatuses connected to the network such as wired/wireless LAN through the communicator 115. The communication interface of short distance wireless communication such as Near Field Communication (NFC) and Bluetooth (Registered trademark) can be applied as the communicator 115.

By executing various programs such as the imaging program, the processor 111 functions as a display controller 111A, an imaging condition setter 111B, an X-ray image obtainer 111C, and an examination order obtainer 111D. The imaging condition setter 111B includes an irradiating parameter selector 111E and a transmitting controller 111F. The above functions are described in detail according to the flowchart shown in FIG. 5. For example, the imaging program is stored in the ROM of the processor 111.

When the X-ray imaging is performed by the X-ray imaging system 1, the registration of the examination order is performed in the imaging control apparatus 11 (examination order obtainer 111D). The registered examination order is displayed on the display 113 of the imaging control apparatus 11 (see FIG. 7). The examination order can be input from the external system such as HIS 32 or RIS 33, or the user can manually input the examination order through the operator 114. Here, the examination order is input from an external system such as the HIS 32 or RIS 33.

When an instruction is made to execute the registered examination order, the imaging condition included in the examination order is transmitted to the X-ray generating control apparatus 21 and the FPD 12 and set (imaging condition setter 111B). The user may change the setting of the irradiating parameter and make minor adjustments through the X-ray generating console 22. When the setting of the irradiating parameter is changed, the signal showing the setting change and the changed irradiating parameter are transmitted to the imaging control apparatus 11 from the X-ray generating control apparatus 21.

When the first stage of pressing the irradiating switch 23 is performed by the user, the warmup of the X-ray tube apparatus 25 (heating of filament) starts. With this, a ready signal (irradiating preparation start signal) which shows that the warmup started is transmitted from the X-ray generating control apparatus 21 to the imaging control apparatus 11. When the ready signal is received, the imaging control apparatus 11 instructs preparation for imaging (initialize) to the FPD 12.

When the warmup of the X-ray tube apparatus 25 ends, the start signal (irradiating preparation complete signal) showing that the warmup is complete is transmitted to the imaging control apparatus 11 from the X-ray generating control apparatus 21. Moreover, an OK signal (imaging preparation complete signal) showing that the imaging preparation is complete is transmitted to the imaging control apparatus 11 from the FPD 12.

When the second stage of pressing the irradiating switch 23 is performed by the user, the X-ray generating control apparatus 21 transmits the X-ray irradiating signal which instructs irradiating of the X-ray to the high voltage generating apparatus 24 and the imaging control apparatus 11. The high voltage generating apparatus 24 applies the high voltage to the X-ray tube apparatus 25, and the irradiating of the X-ray starts. The second stage of pressing the irradiating switch 23 may be performed before receiving the start signal from the X-ray generating control apparatus 21 and the OK signal from the FPD 12. In this case, when the start signal and the OK signal is received, the X-ray irradiating signal is transmitted from the X-ray generating control apparatus 21.

When the irradiating duration is set as in the simple X-ray imaging, when the predetermined irradiating duration passes, the irradiating of the X-ray ends. In the dynamic imaging, during the term that the second stage of pressing the irradiating switch 23 is performed, the irradiating of the X-ray is performed continuously. When the pressing of the irradiating switch 23 is released, the irradiating of the X-ray ends. When the X-ray irradiating ends, the X-ray irradiating signal turns off, and the OK signal, start signal, and the ready signal are also sequentially turned off.

The imaged X-ray image is transmitted from the FPD 12 to the imaging control apparatus 11, and is stored in the storage 112. In the imaging control apparatus 11, various image processing such as offset correction and gain correction are performed on the X-ray image data, and the result is displayed on the display 113 (display controller 111A).

Figure 4:
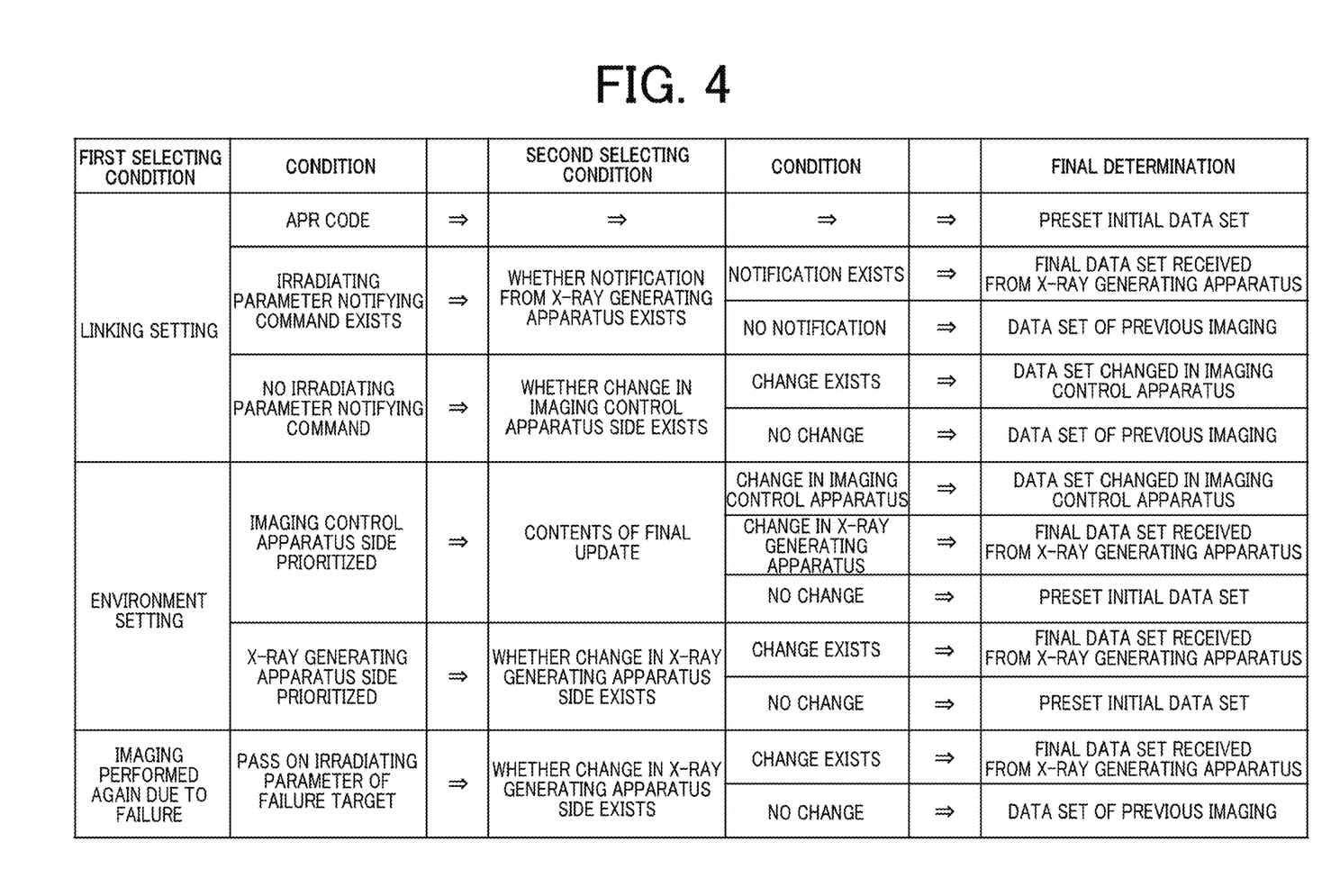
FIG. 4 is a table showing an example of an irradiating parameter selecting table to select an irradiating parameter.

Next, the irradiating parameter selecting table 112C is described.

FIG. 4 is an example of an irradiating parameter selecting table 112C used in the irradiating parameter setting process in the imaging control apparatus 11. The setting of the selection condition and the priority is performed by the person who performs the imaging by using the operator 114 in the imaging control apparatus 11.

The irradiating parameter selecting table 112C shown in FIG. 4 is a layered structure with two layers including a first selecting condition and a second selecting condition.

More specifically, an example in which a "linking setting" is set as the first selecting condition is described.

First, the processor 111 determines the condition that the "linking setting" applies to from "APR code", "irradiating parameter notifying command exists", and "no irradiating parameter notifying command".

When it is determined that the "linking setting" applies to "APR code", the irradiating parameter is determined to be "preset initial data set".

When it is determined that the "linking setting" applies to "irradiating parameter notifying command exists", the processor 111 makes a determination using the second selecting condition "whether notification from X-ray generating apparatus exists". When the second selecting condition is "notification exists", the irradiating parameter is determined to be "final data set received from X-ray generating apparatus". When "notification does not exist", the irradiating parameter is determined to be "data set of previous imaging".

When it is determined that the "linking setting" applies to "no irradiating parameter notifying command", the processor 111 makes a determination using the second selecting condition "whether change in the imaging control apparatus side exists". When the second selecting condition is "change exists", the irradiating parameter is determined to be "data set changed in the imaging control apparatus". When there is "no change", the irradiating parameter is determined to be "data set of previous imaging".

Next, an example in which "environment setting" is set as the first selecting condition is described. The "environment setting" is the place where the operation to change the irradiating parameter is performed.

First, the processor 111 determines the condition that the "environment setting" applies to from "imaging control apparatus side prioritized", and "X-ray generating apparatus side prioritized".

When it is determined that the "environment setting" applies to "imaging control apparatus side prioritized", the processor 111 makes a determination using the second selecting condition "contents of final update". When the second selecting condition is "change in imaging control apparatus", the irradiating parameter is determined to be "data set changed imaging control apparatus". When the second selecting condition is "change in X-ray generating apparatus", the irradiating parameter is determined to be "final data set received from X-ray generating apparatus". When the second selecting condition is "no change", the irradiating parameter is determined to be "preset initial data set".

When it is determined that the "environment setting" applies to "X-ray generating apparatus side prioritized", the processor 111 makes a determination using the second selecting condition "whether change in the X-ray generating apparatus side exists". When the second selecting condition is "change exists", the irradiating parameter is determined to be "final data set received from X-ray generating apparatus". When the second selecting condition is "no change", the irradiating parameter is determined to be "preset initial data set".

Next, an example in which the first selecting condition is "imaging performed again due to failure" is described.

When it is determined that the first selecting condition is "imaging performed again due to failure", the irradiating parameter of a target of failure is continued and passed on.

Next, the processor 111 makes a determination using the second selecting condition "whether change in the X-ray generating apparatus side exists". When the second selecting condition is "change exists", the irradiating parameter is determined to be "final data set received from X-ray generating apparatus". When the second selecting condition is "no change", the irradiating parameter is determined to be "data set of previous imaging".

The above describes the case in which the linking setting, the environment setting, and the imaging performed again due to failure are separately set as the first selecting condition. Alternatively, when the above are not separate, and the "linking setting" is applied but the corresponding irradiating parameter cannot be selected, next, the "environment setting" is applied and the irradiating parameter is selected.

As the second selecting condition, the data set which is updated last is used as the irradiating parameter, and the second selecting condition is selected depending on the time that the irradiating parameter is registered.

The selecting condition is two layers but may be three or more layers.

Figure 5:
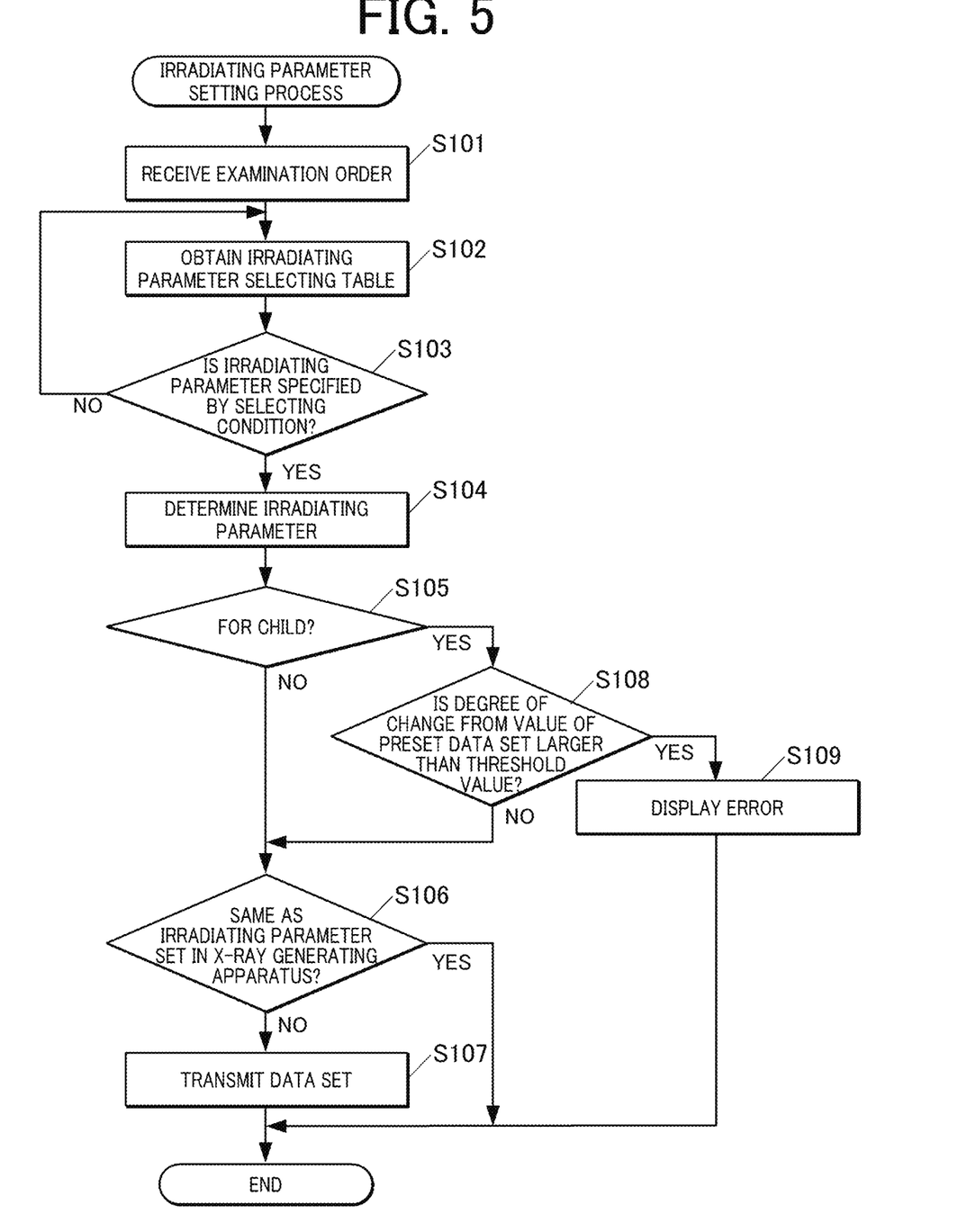
FIG. 5 is a diagram showing a flow which specifies the irradiating parameter.

FIG. 5 is a flowchart showing an example of an irradiating parameter setting process in the imaging control apparatus 11. This process is executed when an instruction is made to execute the examination order in the X-ray imaging by the X-ray imaging system 1 and the irradiating parameter setting program stored in the storage 112 is executed by the processor 111 so that the processor functions as the irradiating parameter selector 111E.

In step S101, the processor 111 receives the examination order selected by the person who performs the imaging using the operator 114 in the imaging control apparatus 11.

In step S102, the processor 111 obtains the selecting condition from the irradiating parameter selecting table 112C stored in the storage 112.

In step S103, the processor 111 specifies the irradiating parameter based on the selecting condition obtained in step S102. When the irradiating parameter cannot be specified (step S103; NO), the selecting condition is changed and the process of step S103 is performed again.

When the irradiating parameter can be specified in step S103 (step S103; YES), in step S104, the processor 111 determines the irradiating parameter.

In step S105, the processor 111 determines whether the examination order is for a child. If the examination order is for a child (step S105; YES), the process proceeds to step S108. If it is not (step S105; NO), the process proceeds to step S106.

In step S106, the processor 111 determines whether the irradiating parameter determined in step S104 is the same as the irradiating parameter set in the X-ray generating apparatus 20. When it is determined that it is the same (step S106; YES), the processor 111 ends the process, and when it is determined that it is not the same (step S106; NO), the process proceeds to step S107.

In step S107, the processor uses the irradiating parameter selector 111E, and transmits the data set of the irradiating parameter determined in step S104 from the imaging control apparatus 11 to the X-ray generating control apparatus 21.

In step S108, the processor 111 determines whether a degree of the change of the value in the data set of the irradiating parameter determined in step S104 from the value in the preset data set is larger than a threshold value. When it is determined that the degree is larger than the threshold value (step S108; YES), the process proceeds to step S109, and when it is not, the process proceeds to step S106.

In step S109, the processor 111 displays that there is an error on the display 113.

In step S105, according to the above description, the process branches depending on whether the examination order is for a child or not, but the condition is not limited to the examination order being for a child. The branch can be set depending on site, modality, imaging condition, and the like.

The threshold value of the degree of change can be set according to the site, modality, and imaging condition.

For example, when the imaging site is set to be a "child", the exposure amount (mAs) and the exposure duration (msec) cannot be increased to a value lager than the preset value or equal to or more than a certain degree.

For example, when the imaging site is set to be a "child", and the grid filling state is ON, it is displayed that there is an error.

For example, if the SID is larger or smaller than the preset value in a certain degree, it is displayed that there is an error.

In step S109, it is displayed that there is an error on the display 113, however, other measures can be used if the person who performs the imaging is notified of the error. For example, a warning lamp can be included in the X-ray imaging apparatus 10, and the error can be notified to the person who performs the imaging.

Figure 6:
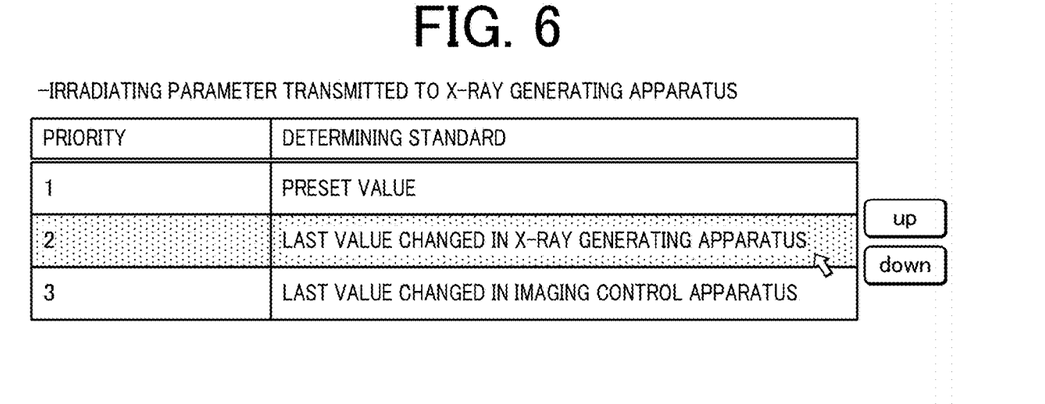
FIG. 6 is a diagram showing an image of a priority setting screen.

FIG. 6 is an image diagram showing a priority setting screen displayed on the display 113 of the imaging control apparatus 11. The person who performs the imaging views the display 113 and uses the operator 114 to perform the setting of the priority.

In FIG. 6, "the last value changed in the X-ray generating apparatus" is selected, and the "final data set received from the X-ray generating apparatus" is prioritized.

The reason why "last" is attached to the selected item is described.

First, as the premise, there are two patterns in which the data set of the irradiating parameter changed in the X-ray generating apparatus 20 and received from the X-ray generating apparatus 20 is held by the imaging control apparatus 11. One pattern is only the last received data set is held (pattern 1) and the other is a plurality of datasets are held for each changed time (pattern 2).

In pattern 2, a plurality of data sets are held. Therefore, in order to specify one, it is necessary to add "last". Alternatively, instead of "last", "second from last" or "first" can be added.

In pattern 1, there is no need to add "last".

There is a pattern in which the imaging control apparatus 11 holds the data set of the irradiating parameter changed in the X-ray generating apparatus 20 and received from the X-ray generating apparatus 20 but the held data is lost due to rebooting of the console.

In this case, after the rebooting of the console, the data set is not changed. Therefore, the first selecting condition "environment setting" is "X-ray generating apparatus side prioritized", the second selection condition "whether change in the X-ray generating apparatus side exists" is "no change", and the "preset initial data set" is selected and set.

Figure 7:
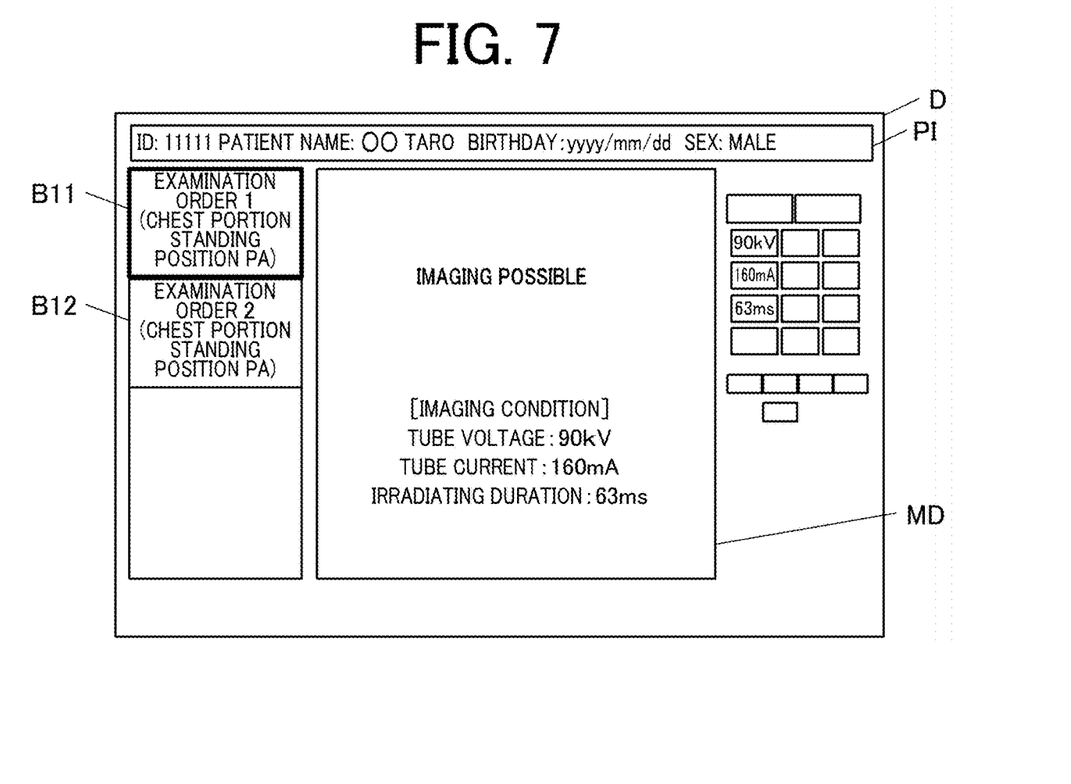
FIG. 7 is a diagram showing an example of a display screen when an instruction is input to execute an examination order.

FIG. 7 is a diagram showing an example of a display screen displayed on the display 113 of the imaging control apparatus 11 when the examination order is executed. According to the example shown in FIG. 7, the person who performs the imaging selects the button B11 and a search order 1 (chest portion standing position PA) is executed.

Figure 8:
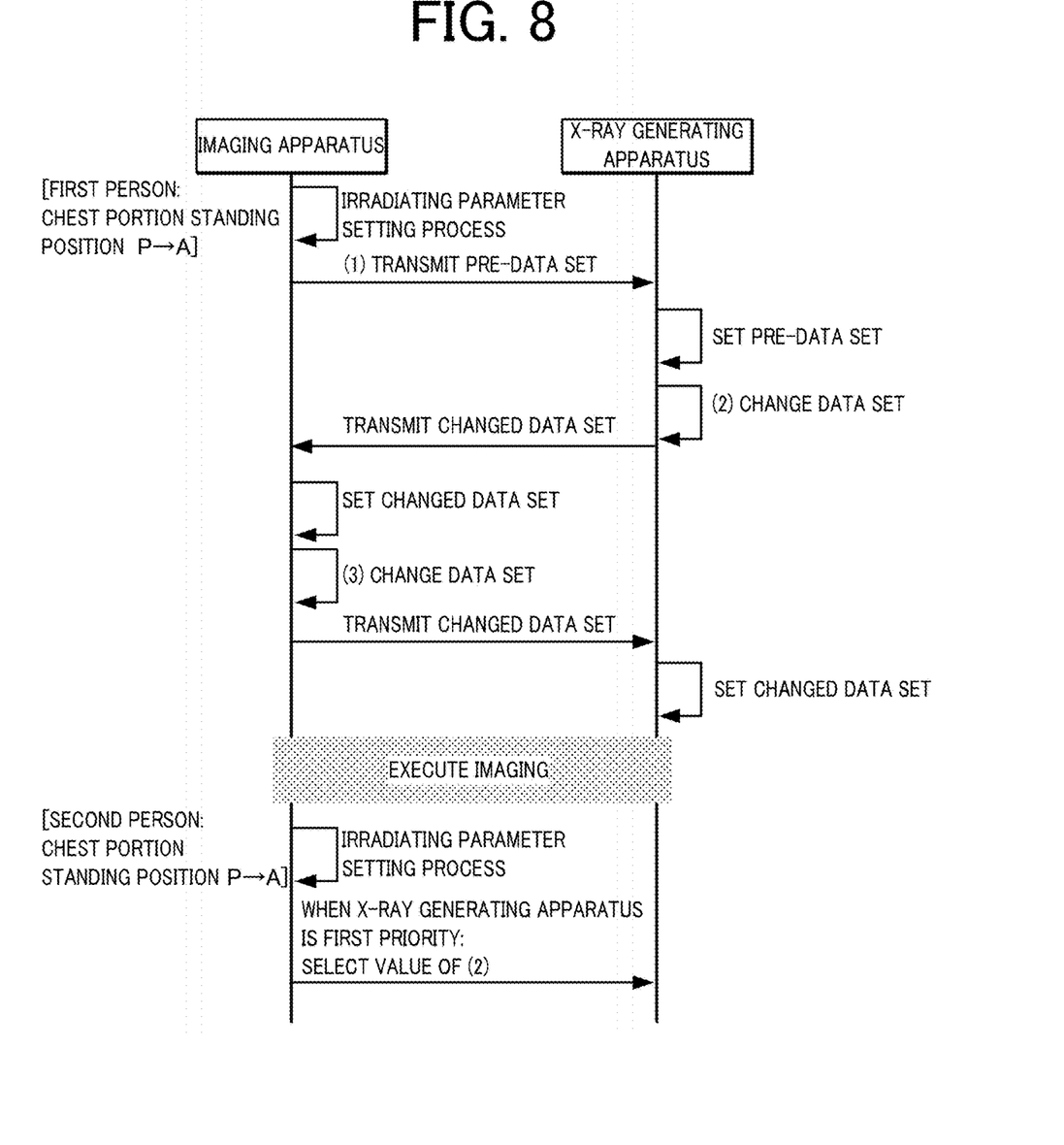
FIG. 8 is an example of a sequence diagram showing a flow of transmitting and receiving an irradiating parameter between an imaging control apparatus and an X-ray generating apparatus.
Figure 9:
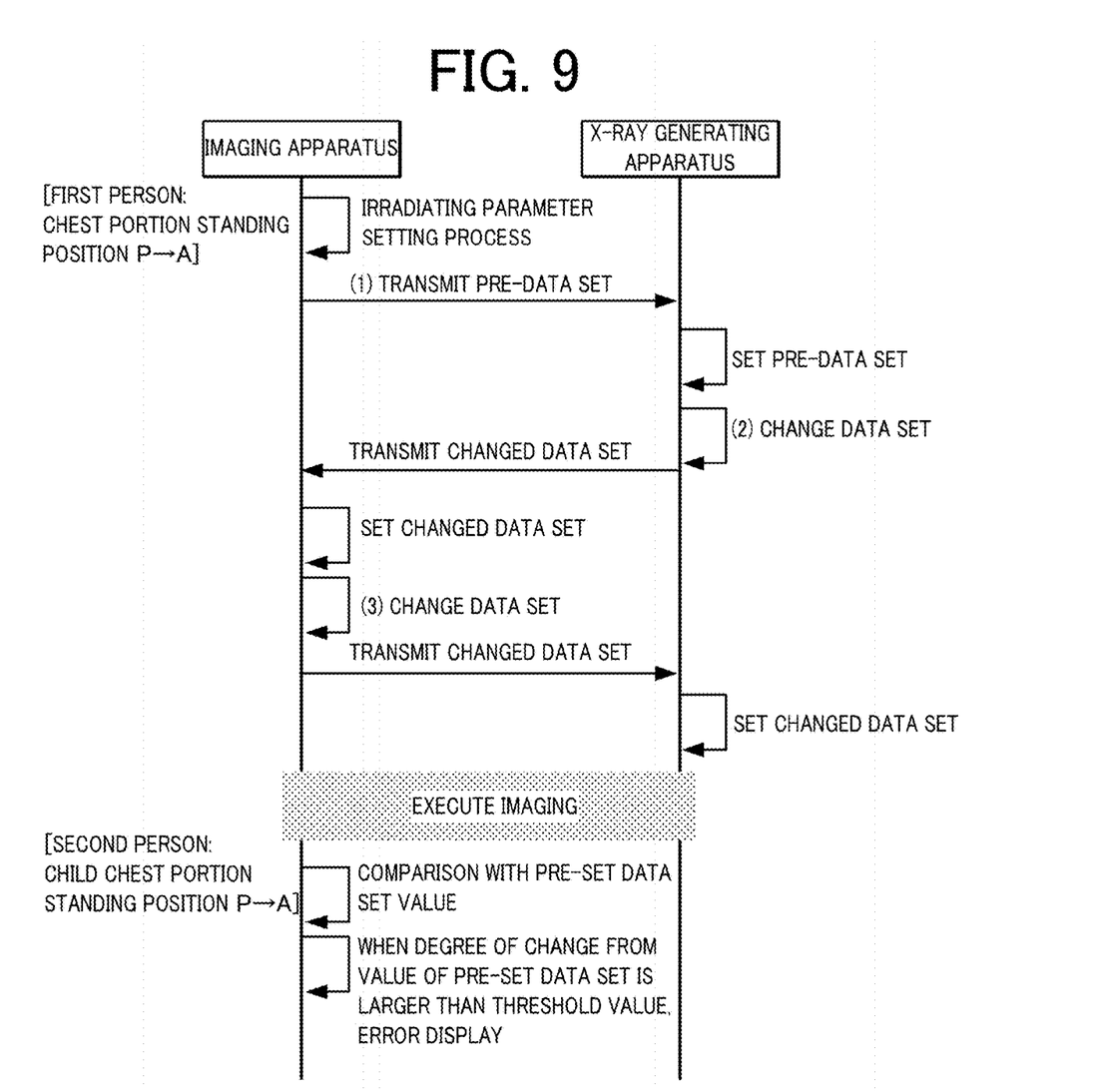
FIG. 9 is an example (child imaging) of a sequence diagram showing a flow of transmitting and receiving an irradiating parameter between an imaging control apparatus and an X-ray generating apparatus.
Figure 10:
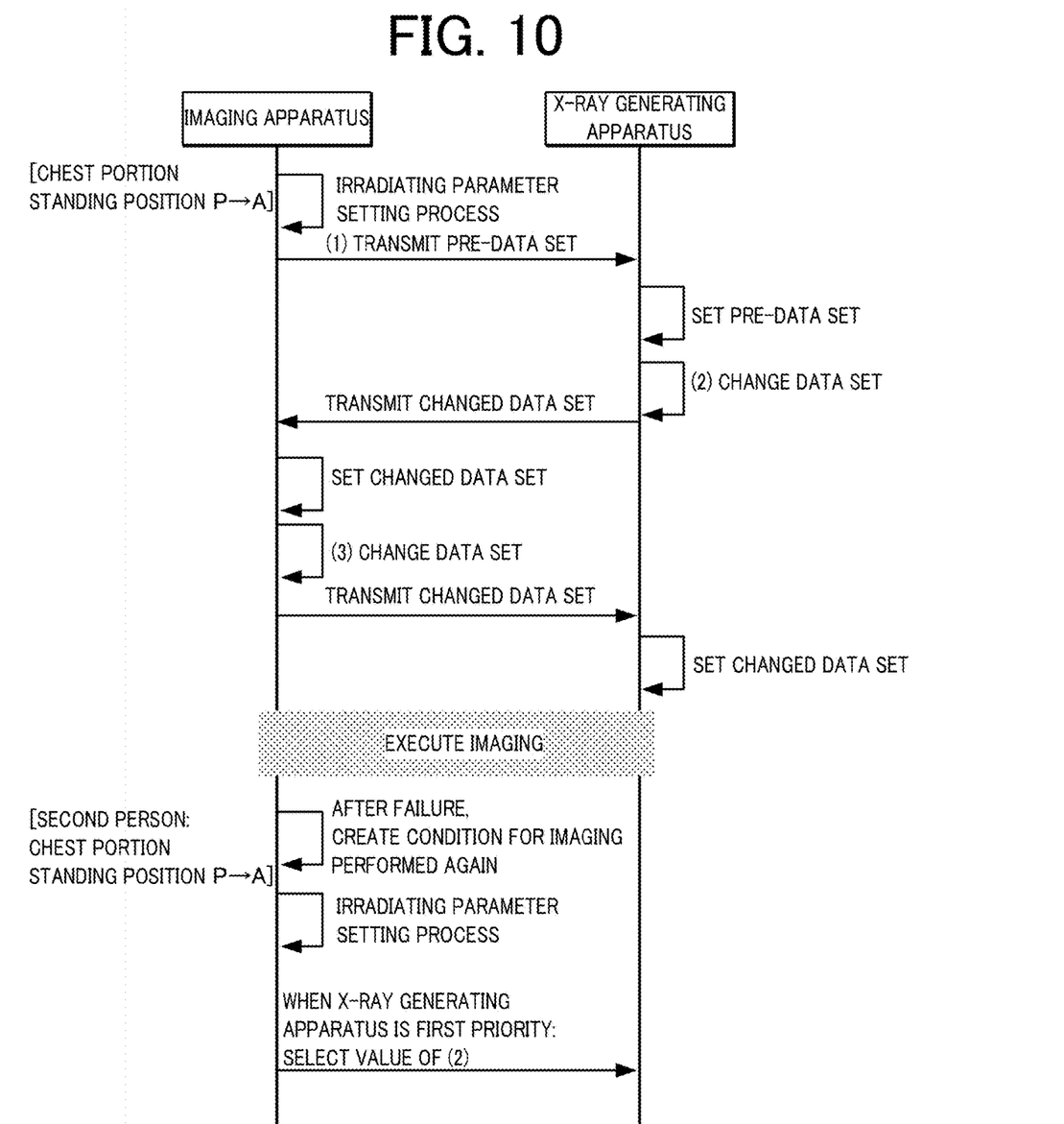
FIG. 10 is an example (failure) of a sequence diagram showing a flow of transmitting and receiving an irradiating parameter between an imaging control apparatus and an X-ray generating apparatus.

Next, with reference to FIG. 8, FIG. 9, and FIG. 10, specific examples of the irradiating parameter setting process when the priority is set as in FIG. 6 and the examination order is selected as in FIG. 7.

FIG. 8 is a sequence diagram showing communication of information between the X-ray generating apparatus 20 and the imaging control apparatus 11 in a situation when examination of "chest portion standing position P to A" is performed for two people successively, the X-ray generating apparatus 20 handles the irradiating parameter notifying command and the X-ray generating apparatus 20 in the "environment setting" is the first setting condition. In the present example, the examination is the first examination from the initial state.

The examination of the first person is described. The irradiating parameter setting process performed in the processor 111 of the imaging control apparatus 11 for the examination of the first person is described with reference to FIG. 4 and FIG. 5.

First, in step S101, when the person who performs the imaging inputs an instruction to execute the examination order in the imaging control apparatus 11, the processor 111 of the imaging control apparatus 11 receives the examination order.

In step S102 of the present example, the situation is that the X-ray generating apparatus 20 handles the irradiating parameter notifying command, and the X-ray generating apparatus 20 in the "environment setting" is the first setting condition. Therefore, the processor 111 obtains the condition in which the first selecting condition is the "environment setting" in the irradiating parameter selecting table 112C shown in FIG. 4.

In step S103, in the present example, the X-ray generating apparatus 20 is the first selecting condition, and the processor 111 selects the condition "X-ray generating apparatus side prioritized". However, the processor 111 cannot specify the irradiating parameter and performs the process in step S102 again.

Since the condition "X-ray generating apparatus side prioritized" is obtained in step S102 the first time, the processor 111 in step S102 the second time obtains the condition in which the second selecting condition is "whether change in the X-ray generating apparatus side exists".

Since there is no change in the irradiating parameter in the X-ray generating control apparatus 21, the processor 111 selects the condition "no change" in step S103 the second time. The processor 111 is able to specify "preset initial data set" as the final decision, and the process proceeds to step S104.

In step S104, the processor 111 determines the irradiating parameter to be "preset initial data set".

In step S105, the processor 111 determines that the examination order in the present example is "chest portion standing position P to A", and this is not for a child. Therefore, the process proceeds to step S106.

In step S106, the processor 111 determines the irradiating parameter to be the "preset initial data set", and the examination is the first examination from the initial state. Therefore, since the data set of the irradiating parameter is not set in the X-ray generating apparatus, the process proceeds to step S107.

In step S107, the processor 111 uses the irradiating parameter selector 111E, and transmits the determined irradiating parameter "preset initial data set" (hereinafter referred to as pre-data set) from the imaging control apparatus 11 to the X-ray generating apparatus 20 (FIG. 8 (1)). The pre-data set is set in the X-ray generating apparatus 20.

Next, when the person who performs the imaging uses the X-ray generating console 22 in the X-ray generating apparatus 20 and changes the data set of the irradiating parameter (FIG. 8 (2)), the changed data set is transmitted from the X-ray generating apparatus 20 to the imaging control apparatus 11. Then, the changed data set is set in the imaging control apparatus 11.

Then, the person who performs the imaging changes the data set of the irradiating parameter in the imaging control apparatus 11 (FIG. 8 (3)). The changed data set is transmitted from the imaging control apparatus 11 to the X-ray generating apparatus 20. Then, the changed data set is set in the X-ray generating apparatus 20. Then, the imaging of the first person is performed.

In the examination of the second person, the irradiating parameter setting process performed in the processor 111 of the imaging control apparatus 11 is described with reference to FIG. 4 and FIG. 5.

First, in step S101, when the instruction to execute the examination order is input by the person who performs the imaging on the imaging control apparatus 11, the processor 111 of the imaging control apparatus 11 receives the examination order.

In step S102, according to the present example, the situation is that the X-ray generating apparatus 20 handles the irradiating parameter notifying command and the X-ray generating apparatus 20 in the "environment setting" is the first selecting condition, the processor 111 obtains the condition in which the first setting condition is the "environment setting" in the irradiating parameter selecting table 112C shown in FIG. 4.

In step S103, in the present example, the X-ray generating apparatus 20 is the first selecting condition, and the processor 111 selects the condition "X-ray generating apparatus side prioritized". However, the processor 111 is not able to specify the irradiating parameter and performs the process in step S102 again.

Since the condition "X-ray generating apparatus side prioritized" is selected in step S102 the first time, the processor 111 obtains the condition of the second selecting condition "whether change in the X-ray generating apparatus side exists" in step S102 the second time.

Since the change of the irradiating parameter is performed in the X-ray generating apparatus 20 in FIG. 8(2) in the present example, the processor 111 selects the condition "change exists" in step S103 the second time. The processor 111 is able to specify "final data set received from the X-ray generating apparatus" as the final decision and the process proceeds to step S104.

In step S104, the processor 111 determines the irradiating parameter to be the "final data set received from the X-ray generating apparatus".

In step S105, the processor 111 determines that the examination order in the present example is the "chest portion standing position P to A" and the examination is not performed on the child. With this, the process proceeds to step S106.

In step S106, the processor 111 determines that the irradiating parameter is the "final data set received from the X-ray generating apparatus" or the data set of the irradiating parameter set in the X-ray generating apparatus is the data set changed in the imaging control apparatus 11. With this, the process proceeds to step S107.

In step S107, the processor 111 uses the irradiating parameter selector 111E and transmits the "final data set received from the X-ray generating apparatus" which is determined to be the irradiating parameter from the imaging control apparatus 11 to the X-ray generating apparatus 20.

The above describes a situation in which the X-ray generating apparatus 20 is the first selecting condition, but when the first selecting condition is the preset value (APR code), the irradiating parameter determined in step S104 is to be the "preset initial data set".

When the first selecting condition is the imaging control apparatus 11, the irradiating parameter determined in step S104 is to be the "data set changed in the imaging control apparatus".

In the above example, the data set of the irradiating parameter is changed in the imaging control apparatus 11 and the X-ray generating apparatus 20. The value held by the imaging control apparatus 11 is the preset initial data set, the data set changed in the X-ray generating apparatus 20, the data set of the previous imaging, and the data set changed in the imaging control apparatus 11, and the number of data held is maximum.

Moreover, in the imaging control apparatus 11, the values can be stored and managed according to type so that the comparison (including display) of each value is possible.

As described above, according to the imaging control apparatus 11 and the irradiating parameter determining method, the parameter for irradiating the radiation suitable for the examination order can be selected.

FIG. 9 is a sequence diagram showing the communicating of information between the X-ray generating apparatus 20 and the imaging control apparatus 11 in a situation in which after the examination of "chest portion standing position P to A" is performed, the examination of "child chest portion standing position P to A" is performed and the X-ray generating apparatus 20 handles the irradiating parameter notifying command, and the X-ray generating apparatus 20 in the "environment setting" is in the first selecting condition. The present example is the first examination from the initial state.

The examination for the first person is the same as the example in FIG. 8, and the description is omitted.

The examination for the second person is the same as the example in FIG. 8 up to step S104, and the description is omitted.

In step S105, since the examination for the second person is the examination of "child chest portion standing position P to A", the processor 111 determines that this is an examination for a child, and the process proceeds to step S108.

In step S108, the value of the irradiating parameter "final data set received from the X-ray generating apparatus" determined in step S104 is compared with the value of the preset data set. The degree of change from the value of the preset data set is calculated, and when the degree exceeds the threshold value, a display showing that there is an error is displayed on the display 113.

With this, it is possible to prevent a child being exposed to a radiation dose that is unacceptable.

FIG. 10 is a sequence diagram showing the communicating of information between the X-ray generating apparatus 20 and the imaging control apparatus 11 in a situation in which the examination of the "chest portion standing position P to A" is considered to be failure after imaging, and the X-ray generating apparatus 20 handles the irradiating parameter notifying command and the X-ray generating apparatus 20 in the "environment setting" is the first selecting condition. In the present example, the examination is to be the first examination from the initial state.

The examination of the first person is the same as FIG. 8, and the description of the present example is omitted.

When the examination of the first person is a failure, the condition to perform the imaging again is created.

Regarding the irradiating parameter in the condition of the imaging performed again, in step S102, with the first selecting condition being the "imaging performed again due to failure", and the second selecting condition being "whether change in the X-ray generating apparatus side exists", the passing on of the irradiating parameter of the target considered to be failure, the change in the X-ray generating apparatus and the irradiating parameter setting process is performed, and according to the present example, the irradiating parameter "final data set received from the X-ray generating apparatus" is transmitted.

As described above, even if there is failure, the suitable irradiating parameter of the radiation can be selected.

OTHER EXAMPLES

When the order is switched, it is possible to identify which type of values the irradiating parameter selected at present is using (sending to generating apparatus side).

When the order is switched, in addition to which type of values the irradiating parameter selected at present is using (sending to generating apparatus side), it is possible to identify the degree of change by displaying the initial preset value in an aligned state.

With this, even if it is not determined to be an error according to the threshold value described above, the degree of change can be understood, and it is possible to prevent exposure to unacceptable radiation dose.

When one examination is completed, the user is able to determine whether to update the value of the preset data set to the final changed value (value used in imaging) or the priority of the rules for updating and storing can be specified in advance.

For each imaging, the values of the data set of the final irradiating parameter selected based on the priority rule and the preset initial data set can be stored associated with the examination information, displayed as a list or output. With this, the above can be used to improve the preset initial data set.

When the imaging condition for imaging again is added when the imaging is performed again after determining that the imaging is a failure after imaging, the irradiating parameter is selected according to the priority.

For example, when the final irradiating parameter in the previous imaging is changed in the X-ray generating apparatus side, the irradiating parameter received from the X-ray generating apparatus is selected. When the APR code is used, the imaging condition of the target of failure is passed on as is.

Although embodiments of the present invention have been described and illustrated in detail, the disclosed embodiments are made for purposes of illustration and example only and not limitation. The scope of the present invention should be interpreted by terms of the appended claims and its equivalents.

What is claimed is:

1. A radiation imaging control apparatus comprising:
   a hardware processor; and
   an operator,
   wherein,
   the hardware processor obtains an examination order and one or a plurality of radiation irradiating parameters corresponding to each examination order,
   the examination order to be executed and a selecting condition of a plurality of selecting conditions are selected using the operator,
   when the examination order is selected on the operator, the hardware processor determines a condition to which the selecting condition is according to a priority setting, and selects a radiation irradiating parameter for the examination order from the one or the plurality of radiation irradiating parameters according to the determined condition of the selecting condition, and
   the priority setting is determined by a user input operation on the operator.

2. The radiation imaging control apparatus according to claim 1, wherein the hardware processor transmits the selected radiation irradiating parameter to the radiation generating apparatus, and
   when the selected radiation irradiating parameter is already set in the radiation generating apparatus, the selected radiation irradiating parameter is not transmitted.

3. The radiation imaging control apparatus according to claim 1, wherein,
   the priority setting includes a plurality of layers,
   the selecting condition includes a first selecting condition and a second selecting condition, and the hardware processor determines a condition of the first selecting condition based on the priority setting of a first layer, and the hardware processor determines a condition of the second selecting condition based on the priority setting of a second layer.

4. The radiation imaging control apparatus according to claim 1,
   wherein, the hardware processor selects the radiation irradiating parameter according to the priority setting from any one or more of the selecting conditions including, including: linking setting with a radiation generating apparatus, place of operation where the radiation irradiating parameter is changed, time when radiation irradiating parameter is registered, and user selection.

5. The radiation imaging control apparatus according to claim 1, wherein the priority setting is defined by the user input operation of one or more of the plurality of selecting conditions.

6. The radiation imaging control apparatus according to claim 3, wherein the radiation irradiating parameter is any one among a preset initial data set, a data set changed in a radiation generating apparatus, a data set in the previous imaging, and the data set changed in the radiation imaging apparatus.

7. A radiation imaging control apparatus comprising:
   a hardware processor; and
   an operator,
   wherein,
   the hardware processor obtains an examination order and one or a plurality of radiation irradiating parameters corresponding to each examination order,
   the examination order to be executed and a selecting condition of a plurality of selecting conditions are selected using the operator,
   when the examination order after imaging is considered to be a failure and there is a request to perform imaging again, the hardware processor determines a condition to which the selecting condition is applied among a plurality of conditions according to a priority setting, and selects the radiation irradiating parameter of the examination order from the one or the plurality of radiation irradiating parameters according to the determined condition of the selecting condition, and
   the priority setting is determined by a user input operation on the operator.

8. A radiation irradiating parameter determining method comprising:
   obtaining an examination order and one or a plurality of radiation irradiating parameters corresponding to each examination order,
   selecting the examination order to be executed and a selecting condition of a plurality of selecting conditions, when the examination order is selected, determining a condition to which the selecting condition is applied among a plurality of conditions according to a priority setting, and selecting a radiation irradiating parameter for the examination order from the one or the plurality of radiation irradiating parameters according to the determined condition of the selecting condition, and determining a priority setting by a user operation when the examination order is selected.

9. A non-transitory computer-readable storage medium storing a program causing a computer to perform:

obtaining an examination order and one or a plurality of radiation irradiating parameters corresponding to each examination order, selecting the examination order to be executed and a selecting condition of a plurality of selecting conditions, when the examination order is selected, determining a condition to which the selecting condition is applied among a plurality of conditions according to a priority setting, and selecting a radiation irradiating parameter for the examination order from the one or the plurality of radiation irradiating parameters according to the determined condition of the selecting condition, and determining a priority setting by a user operation when the examination order is selected.

* * * * *